(12) United States Patent
Dahl

(10) Patent No.: US 10,633,661 B2
(45) Date of Patent: *Apr. 28, 2020

(54) TREATMENT OF HYPERHIDROSIS

(71) Applicant: HIDROS THERAPEUTICS INTERNATIONAL AB, Uppsala (SE)

(72) Inventor: Niklas Dahl, Uppsala (SE)

(73) Assignee: HIDROS THERAPEUTICS INTERNATIONAL AB, Uppsala (SE)

(*) Notice: Subject to any disclaimer, the term of this patent is extended or adjusted under 35 U.S.C. 154(b) by 0 days.

This patent is subject to a terminal disclaimer.

(21) Appl. No.: 15/709,249

(22) Filed: Sep. 19, 2017

(65) Prior Publication Data

US 2018/0044682 A1 Feb. 15, 2018

Related U.S. Application Data

(62) Division of application No. 14/759,153, filed as application No. PCT/SE2013/051508 on Dec. 13, 2013, now Pat. No. 9,809,820.

(60) Provisional application No. 61/748,592, filed on Jan. 3, 2013.

(51) Int. Cl.
| | | |
|---|---|---|
| C12N 15/113 | (2010.01) | |
| A61K 31/7105 | (2006.01) | |
| A61K 31/713 | (2006.01) | |
| A61K 9/00 | (2006.01) | |
| A61K 9/70 | (2006.01) | |

(52) U.S. Cl.
CPC ........ *C12N 15/1138* (2013.01); *A61K 9/0019* (2013.01); *A61K 9/7023* (2013.01); *A61K 31/713* (2013.01); *A61K 31/7105* (2013.01); *C12N 2310/14* (2013.01)

(58) Field of Classification Search
None
See application file for complete search history.

(56) References Cited

U.S. PATENT DOCUMENTS

| | | | |
|---|---|---|---|
| 9,809,820 B2 * | 11/2017 | Dahl ................ | A61K 31/7105 |
| 2004/0138187 A1 | 7/2004 | Reading et al. | |
| 2007/0191294 A1 | 8/2007 | Elmen et al. | |
| 2008/0113351 A1 | 5/2008 | Naito et al. | |
| 2012/0207704 A1 | 8/2012 | Jacky et al. | |

FOREIGN PATENT DOCUMENTS

| | | |
|---|---|---|
| WO | WO 02/11690 A1 | 2/2002 |
| WO | WO 2007/046102 A2 | 4/2007 |
| WO | WO 2009/051818 A1 | 4/2009 |
| WO | WO 2010/065567 A2 | 6/2010 |
| WO | WO 2011/020114 A2 | 2/2011 |

OTHER PUBLICATIONS

Arguin, Guillaume et al.; "Protein kinase C phosphorylates the inositol 1,4,5-trisphosphate receptor type 2 and decreases the mobilization of $Ca^{2+}$ in pancreatoma AR4-2J cells"; Journal of Endocrinology; 192; 2007; pp. 659-668.

Arote, Rohidas B. et al.; "Degradable poly(amido amine)s as gene delivery carriers"; Expert Opinion on Drug Delivery; 8:9; 2011; pp. 1237-1246.

Burnett, John C. et al.; "RNA-based Therapeutics—Current Progress and Future Prospects"; Chem Biol.; 19(1); Jan. 27, 2012; pp. 60-71.

Distelhorst, Clark W. et al.; "Bcl-2 interaction with the inositol 1,4,5-trisphosphate receptor: role in $Ca^{2+}$ signaling and disease"; Cell Calcium.; 50(3); Sep. 2011; pp. 234-241.

Felgner, Philip L. et al.; "Lipofection: A highly efficient, lipid-mediated DNA-transfection procedure"; Proc Natl. Acad. Sci. USA; vol. 84; Nov. 1987; pp. 7413-7417.

Futatsugi, Akira et al.; "$IP^3$ receptor Types 2 and 3 Mediate Exocrine Secretion Underlying Energy Metabolism"; Science; vol. 309; Sep. 30, 2005; pp. 2232-2234.

Gindy, Marian E. et al.; "Challenges in the pharmaceutical development of lipid-based short interfering ribonucleic acid therapeutics"; Expert Opinion on Drug Delivery; 9(2); 2012; pp. 171-182.

Goemans, Nathalie M. et al.; "Systemic Administration of PRO051 in Duchenne's Muscular Dystrophy"; The New England Journal of Medicine; 364; 16; Apr. 21, 2011; pp. 1513-1522.

James, William et al.; "Disorders of the Sweat Glands"; Andrews' Diseases of the Skin: Clinical Dermatology; (10th ed.); Saunders; 2005; 5pp.

Klar, Joakim, et al.; "Abolished $InsP_3R2$ function inhibits sweat secretion in both humans and mice"; The Journal of Clinical Investigation; vol. 124; No. 11; Nov. 2014; pp. 4773-4780.

Lara, Maria Fernanda et al.; "Inhibition of CD44 Gene Expression in Human Skin Models, Using Self-Delivery Short Interfering RNA Administered by Dissolvable Microneedle Arrays"; Human Gene Therapy; 23; 2012; pp. 1-8.

Leachman, Sancy A. et al.; "First-in-human Mutation-targeted siRNA Phase Ib Trial of an Inherited Skin Disorder"; Molecular Therapy; vol. 18; No. 2; Feb. 2010; pp. 442-446.

Li, Mingjie et al.; "Lentiviral Vector Delivery of siRNA and shRNA Encoding Genes into Cultured and Primary Hematopoietic Cells"; Methods in Molecular Biology 433; Chapter 18; Gene Therapy Protocols; vol. 1; 2008; pp. 287-299.

(Continued)

*Primary Examiner* — J. E Angell
(74) *Attorney, Agent, or Firm* — Lewis Roca Rothgerber Christie LLP

(57) ABSTRACT

The present invention relates to a composition for reducing sweating in humans, characterized in that said composition comprises a compound capable of reduction of ITPR2 protein function and reduction of levels of ITPR2 mRNA and/or ITPR2 protein, and optionally pharmaceutically acceptable carriers and/or excipients, as well as to methods of treatment and specific siRNA molecules and their use in therapy.

Figures 1A, 1B:
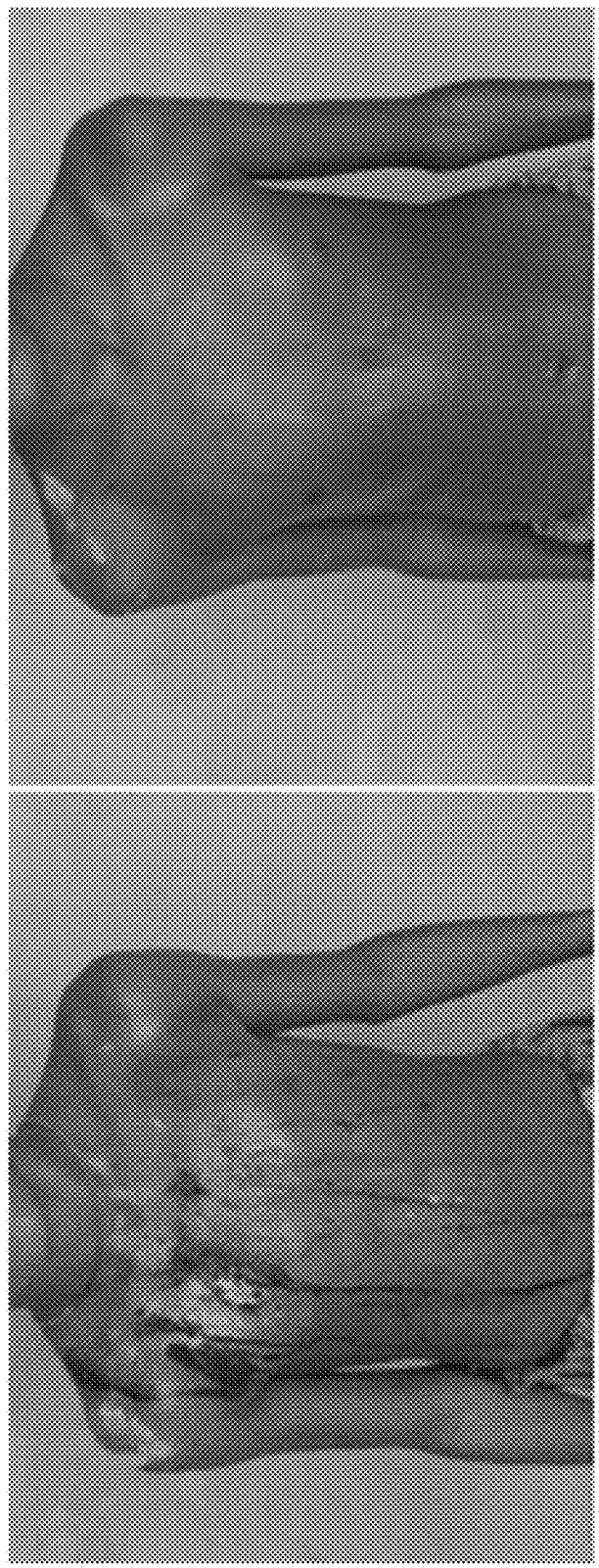

20 Claims, 4 Drawing Sheets
(4 of 4 Drawing Sheet(s) Filed in Color)
Specification includes a Sequence Listing.

(56) References Cited

OTHER PUBLICATIONS

Lin, Chang-Min et al.; "A simple, noninvasive and efficient method for transdermal delivery of siRNA" Arch Dermatol Res; 304; 2012; pp. 139-144.
Suhr, Ole B. et al.; "Efficacy and safety of patisiran for familial amyloidotic polyneuropathy: a phase II multi-dose study"; Orphanet Journal of Rare Diseases; 2015; 10:109; 9pp.
Yule, David I. et al.; "Linking Structure to Function: Recent Lessons from Inositol 1,4,5-trisphosphate Receptor Mutagenesis"; Cell Calcium; 47(6); Jun. 2010; pp. 469-479.
Zhang, Songbai et al.; "G-protein-coupled Receptor Kinase-interacting Proteins Inhibit Apoptosis by Inositol 1,4,5-Trisphosphate Receptor-mediated $Ca^{2+}$ Signal Regulation"; Journal of Biological Chemistry; vol. 284; No. 42; Oct. 16, 2009; pp. 29158-29169.
Office action dated Dec. 26, 2016 in corresponding Chinese Patent Application No. 201380069414.3, including Eng. trans. 16pp.
European Search Report dated Nov. 15, 2016 for corresponding European Patent Application No. 13870321.0, 10pp.
Chia, K.Y. et al.; "Approach to hypohidrosis"; Journal of the European Academy of Dermatology Venerealogy; Oct. 2012; 27; pp. 799-804.
Galeotti, N. et al.; "An antidepressant behaviour in mice carrying a gene-specific InsP3R1, InsP3R2 and InsP3R3 protein knockdown"; Neuropharmacology; 55; 2008; pp. 1156-1164.
International Search Report for PCT/SE2013/051508, dated Mar. 21, 2014, 5 pages.
Written Opinion of the International Searching Authority for PCT/SE2013/051508, dated Mar. 21, 2014, 7 pages.
Office action issued in Japanese Patent Application No. 2015-551659, dated Apr. 21, 2017, 10 pages.
Kruglov, Emma A., "Type 2 Inositol 1,4,5-Trisphosphate Receptor Modulates Bile Salt Export Pump Activity in Rat Hepatocytes," Hepatology, vol. 54, No. 5, 2011, pp. 1790-1799.
Contreras-Ferrat, A.E., et al., "An Inositol 1,4,5-Triphosphate ($IP_3$)-$IP_3$ Receptor Pathway is Required for Insulin-Stimulated Glucose Transporter 4 Translocation and Glucose Uptake in Cardiomyocytes," Endocrinology, Oct. 2010, 151(10), pp. 4665-4677, www.endo.endojournals.org.
Davis, Michael C., et al., "Dexamethasone-induced Inositol 1,4,5-Trisphosphate Receptor Elevation in Murine Lymphoma Cells is Not Required for Dexamethasone-mediated Calcium Elevation and Apoptosis," Journal of Biological Chemistry, vol. 283, No. 16, Apr. 18, 2008, pp. 10357-10365.
Tovey, Stephen C., "Selective Coupling of type 6 adenylyl cyclase with type 2 $IP_3$ receptors mediates direct sensitization of $IP_3$ receptors by cAMP," The Journal of Cell Biology, vol. 183, No. 2, Oct. 20, 2008, pp. 297-312.
Ramos-Franco, Josephina, et al., "Isoform-Specific Function of Single Inositol 1,4,5-Triphosphate Receptor Channels," Biophysical Journal, vol. 75, Aug. 1998, pp. 834-839.
IN Office action dated Jun. 14, 2019 in corresponding Appln No. 5848/DELNP/2015, with English translation, 8 pages.
Ko, Wing Hung, et al., "Extracellular ATP Can Activate Autonomic Signal Transduction Pathways in Cultured Equine Sweat Gland Epithelial Cells", J. Exp. Biol., vol. 190, 1994, pp. 239-252.
Nejsum, Lene N., et al., "Functional Requirement of Aquaporin-5 in Plasma Membranes of Sweat Glands", PNAS, Jan. 8, 2002, vol. 99, No. 1, pp. 511-516.
Vanhouten, Joshua N., et al., "Transcellular Calcium Transport in Mammary Epithelial Cells", J. Mammary Gland Biol. Neoplasia, 2007, vol. 12, pp. 223-235.

* cited by examiner

SEQUENCE LISTING

```
<160> NUMBER OF SEQ ID NOS: 13

<210> SEQ ID NO 1
<211> LENGTH: 19
<212> TYPE: RNA
<213> ORGANISM: Homo sapiens

<400> SEQUENCE: 1
gcuuaauccu gauuaucga                                                  19

<210> SEQ ID NO 2
<211> LENGTH: 19
<212> TYPE: RNA
<213> ORGANISM: Homo sapiens

<400> SEQUENCE: 2
ggugucuaau caagacgua                                                  19

<210> SEQ ID NO 3
<211> LENGTH: 19
<212> TYPE: RNA
<213> ORGANISM: Homo sapiens

<400> SEQUENCE: 3
gcgagagagu uguacaaca                                                  19

<210> SEQ ID NO 4
<211> LENGTH: 25
<212> TYPE: DNA
<213> ORGANISM: Homo sapiens

<400> SEQUENCE: 4
ccagcaacat agagcttctt gataa                                           25

<210> SEQ ID NO 5
<211> LENGTH: 25
<212> TYPE: DNA
<213> ORGANISM: Homo sapiens

<400> SEQUENCE: 5
gaccttgcgc caatcagcta cttct                                           25
```

```
<210> SEQ ID NO 6
<211> LENGTH: 25
<212> TYPE: DNA
<213> ORGANISM: Homo sapiens

<400> SEQUENCE: 6
aagcatcttg caactggaaa ctatt                                     25

<210> SEQ ID NO 7
<211> LENGTH: 25
<212> TYPE: DNA
<213> ORGANISM: Homo sapiens

<400> SEQUENCE: 7
gatgatgaag aagtttggct ctatt                                     25

<210> SEQ ID NO 8
<211> LENGTH: 25
<212> TYPE: DNA
<213> ORGANISM: Homo sapiens

<400> SEQUENCE: 8
cagaaagcct cagtggaatc ctgta                                     25

<210> SEQ ID NO 9
<211> LENGTH: 25
<212> TYPE: DNA
<213> ORGANISM: Homo sapiens

<400> SEQUENCE: 9
ccagtggatt tggacagcca agtta                                     25

<210> SEQ ID NO 10
<211> LENGTH: 25
<212> TYPE: DNA
<213> ORGANISM: Homo sapiens

<400> SEQUENCE: 10
cagtggattt ggacagccaa gttaa                                     25

<210> SEQ ID NO 11
<211> LENGTH: 25
<212> TYPE: DNA
<213> ORGANISM: Homo sapiens

<400> SEQUENCE: 11
cagacattca gtgtctgctg gataa                                     25

<210> SEQ ID NO 12
<211> LENGTH: 25
<212> TYPE: DNA
<213> ORGANISM: Homo sapiens

<400> SEQUENCE: 12
cacatgagtc taatgggatt gatat                                     25

<210> SEQ ID NO 13
<211> LENGTH: 25
<212> TYPE: DNA
<213> ORGANISM: Homo sapiens

<400> SEQUENCE: 13
cggtttcatt tgaggagcac attaa                                     25
```

TREATMENT OF HYPERHIDROSIS

CROSS-REFERENCE TO RELATED APPLICATION(S)

This application is a divisional of U.S. patent application Ser. No. 14/759,153, filed Jul. 2, 2015 which is a National Stage and claims priority and the benefit of International Application No. PCT/SE2013/051508, filed Dec. 13, 2013, which claims priority to and the benefit of U.S. Provisional Application No. 61/748,592, filed Jan. 3, 2013, the entire contents of both of which are incorporated herein by reference.

INCORPORATING BY REFERENCE

The instant application contains a Sequence Listing which has been submitted in ASCII format via eFS-Web and is hereby incorporated by reference in its entirety. Said ASCII copy, was amended on Oct. 30, 2015, is named SEQLISTING78288.txt, and is 2,145 bytes in size.

FIELD OF THE INVENTION

The present invention relates to methods, compounds and compositions for reducing or eliminating sweating and for treatment of excessive sweating, such as hyperhidrosis. In particular it relates to reduction of ITPR2 protein function and reduction of levels of ITPR2 mRNA and/or ITPR2 protein in the secretory part of sweat gland cells causing reduced sweat gland function of a treated subject.

BACKGROUND OF THE INVENTION

Excessive sweating can lead to significant discomfort, both physical and emotional.

Hyperhidrosis is a medical condition in which a person sweats excessively and unpredictably. When excessive sweating affects the hands, feet, and armpits, it's called primary or focal hyperhidrosis. Primary hyperhidrosis affects approximately 2-3% of the population, yet less than 40% of patients with this condition seek medical advice. In the majority of primary hyperhidrosis cases, no cause can be found. The most prevalent form of hyperhidrosis is hyperhidrosis palmoplantaris characterized by excessive sweating of palms, soles and axillae.

If the excessive sweating occurs as a result of another medical condition, it is called secondary hyperhidrosis. The sweating may be generalized (i.e. all over the body), or it may be in a restricted area.

Prevention of excessive sweating can include Botulinum toxin administrated through injections or iontophoresis as well as antiperspirants containing aluminium chloride hexahydrate which plug the sweat ducts and may cause skin irritation. Medical treatments include anticholinergics drugs, such as glycopyrrolate, and tricyclic antidepressants. Both glycopyrrolate and tricyclic antidepressants inhibits acetylcholine on its muscarinic receptors with anticholinergic side effects such as blurred vision, constipation, dry mouth, dizziness, headache, impotence and problems with urination. Excessive sweating may also be treated by surgery and sympathetic denervation.

Inositol 1,4,5-trisphosphate receptor Type 2 (ITPR2) is an intracellular $Ca^{2+}$ release channel that is expressed in many tissues. In mammalians, at least three forms of ITPR are identified assigned type 1, 2 and 3 respectively (Yule, 2010). The ITPR2 channel is a homotetrameric or a heterotetrameric structure with three functional domains; a transmembrane domain containing the $Ca^{2+}$-channel pore close to the COOH-terminus, the amino-terminal IP3 binding domain, and a large cytosolic domain that connects the $Ca^{2+}$ channel with the IP3-binding region. With the exception of the short transmembrane domain containing the $Ca^{2+}$ pore, the major part of the ITPR2 is exposed to the cytoplasm and is a target for several accessory proteins as well as kinases.

No specific human phenotype has been reported as associated with down-regulation of, or mutations in any of the three ITPR2 genes. Furthermore, mice with a targeted disruption of ITPR2 show no abnormal phenotype (Futatsugi, 2005). However, a mouse model with deletion of both the type 2 (ITPR2) and the type 3 (ITPR3) receptor genes show exocrine dysfunction of the salivary and the pancreatic glands (Futatsugi, 2005).

SUMMARY OF THE INVENTION

The present invention aims to provide compounds and compositions for use to reduce or eliminate sweating in a subject, as well as methods using said compounds and compositions to reduce or eliminate sweating in a subject. The subject may be a patient suffering from hyperhidrosis. The subject may also be an individual who is sweating normally or less than normal, with wishes to reduce sweating even further.

Especially suitable subjects are those suffering from hyperhidrosis, a disorder affecting approx 2-3% of the population (James, 2005). The most prevalent form of hyperhidrosis is hyperhidrosis palmoplantaris characterized by excessive sweating of palms, soles and axillae.

One aspect of the invention is to reduce or eliminate sweating based on the unexpected finding that ITPR2 is a crucial part of the pathway regulating sweat gland function and thereby sweating. Any molecule or reagent, single or in combination, that inhibits (partially or completely), antagonizes or reduces ITPR2 function in sweat glands is useful in the present invention. This includes molecules and reagents reducing levels of ITPR2 mRNA, such as siRNA against ITPR2 mRNA; molecules and reagents reducing levels of ITPR2 protein; molecules and reagents reducing ITPR2 calcium channel formation; molecules and reagents reducing ITPR2 calcium channel function.

Indirect perturbation of the ITPR2 protein may be mediated through BCL-2 or ITPR derived peptides (Distelhorst and Bootman, 2011), Protein kinase C (Arguin et al 2007), G-protein-coupled receptor kinase interacting proteins such as GIT1 and GIT2 (Zhang et al 2009).

The main aspects of the invention are disclosed in the independent claims. Preferred embodiments are set forth in the dependent claims.

SHORT DESCRIPTION OF THE APPENDED DRAWINGS

The patent or application file contains at least one drawing executed in color. Copies of this patent or patent application publication with color drawings will be provided by the Office upon request and payment of the necessary fee.

FIGS. 1A and 1B. Illustration of impaired or absent sweating (anhidrosis) caused by non-functional ITPR2. Starch-iod test for the analysis of perspiration in a healthy individual (left) and a patient homozygous for the ITPR2 missense mutation p.G2498S (right) after exposure in 45° C. in a humid environment. An iodine solution is applied to the skin. After drying, starch is sprinkled on the area. The starch-iodine mixture turns into dark blue color in the presence of sweat (left). No color reaction is observed in patient homozygous for the ITPR2 missense mutation p.G2498S (right).

Figures 2A, 2B:
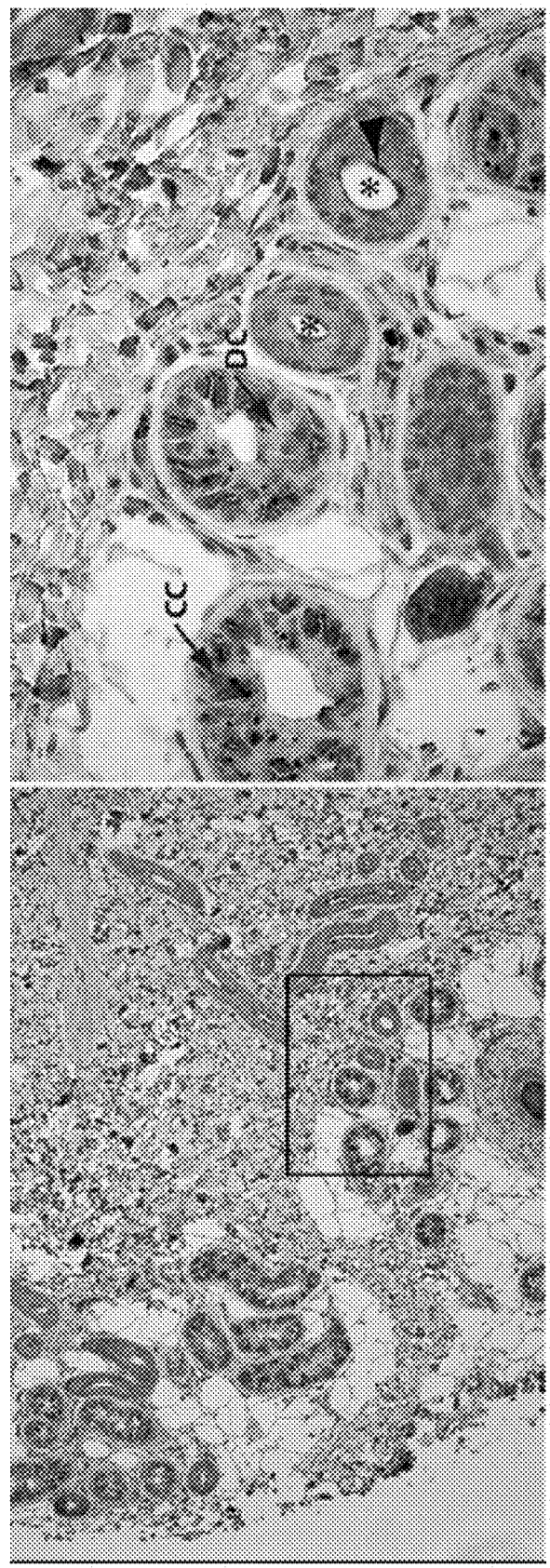

FIGS. 2A and 2B. Immunostaining of ITPR2 in normal skin with sweat gland (boxed). The expression of ITPR2 in eccrine sweat glands corresponds to the brown staining localized mainly in the pyramidal-shaped "clear cells" (CC) of the secretory (sweat producing) portion of the gland (right). The luminar so-called "dark cells" (DC) are not stained. Arrows indicate ITPR2 staining also in the luminal membrane of the duct cells (*). Staining is performed with a polyclonal Rabbit anti-ITPR2 1:1000 (Millipore).

Figure 3:
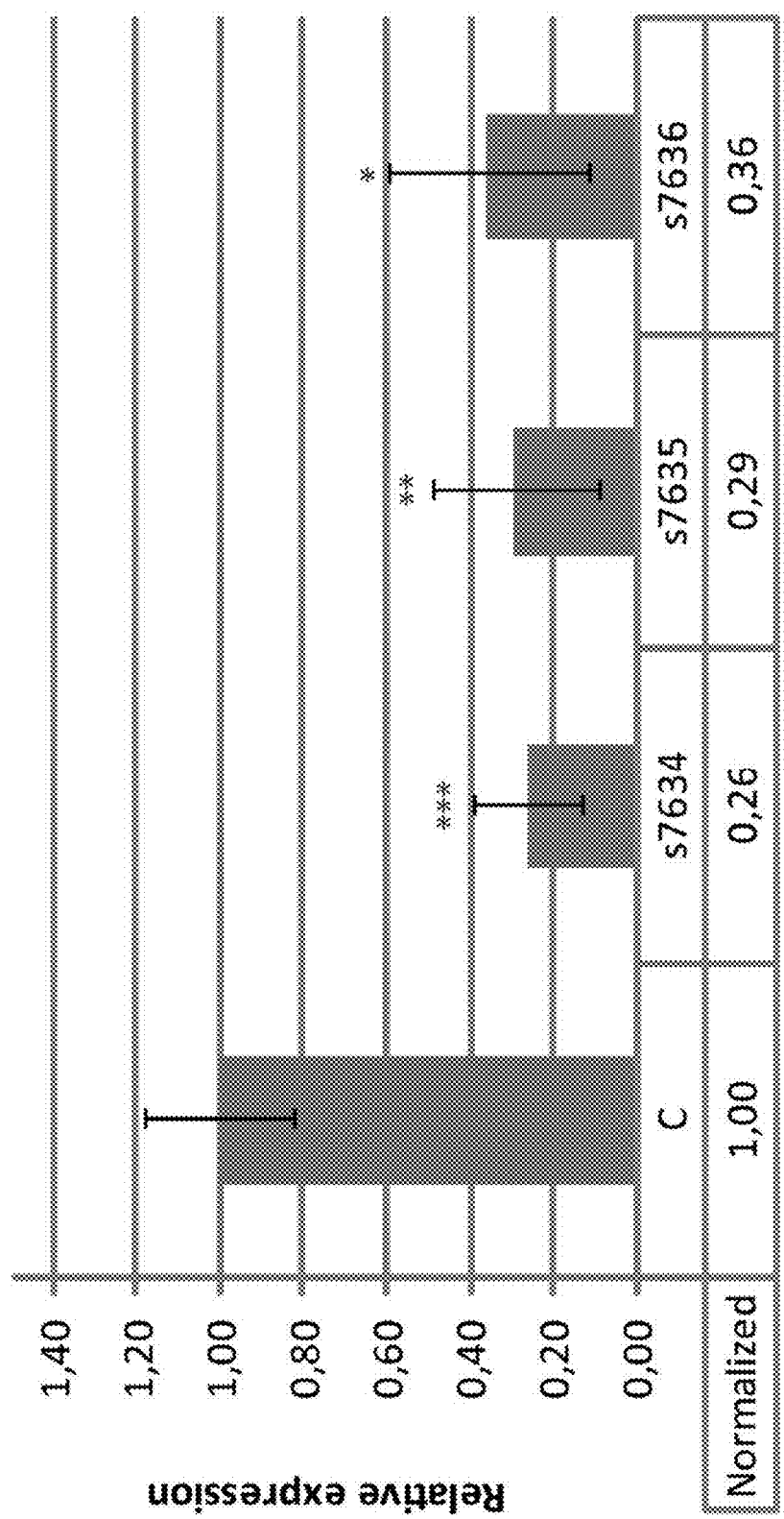

FIG. 3. Down-regulation of ITPR2 mRNA using siRNA (s7634, s7635 and s7636; Ambion) in fibroblast cells. Bars illustrate the relative expression of ITPR2 mRNA, normalized to □-2 micro globulin mRNA in non-induced fibroblasts (left bar; "C") and in fibroblasts after siRNA induction using s7634, s7635 and s7636, respectively. The ITPR2 mRNA levels in non-induced control cells are set to 1 (n=4). The down-regulation of ITPR2 was found significant after induction with s7634 (p=0.0006; n=4), s7635 (p=0.006; n=4) and s7636 (p=0.019; n=2).

Figure 4A:
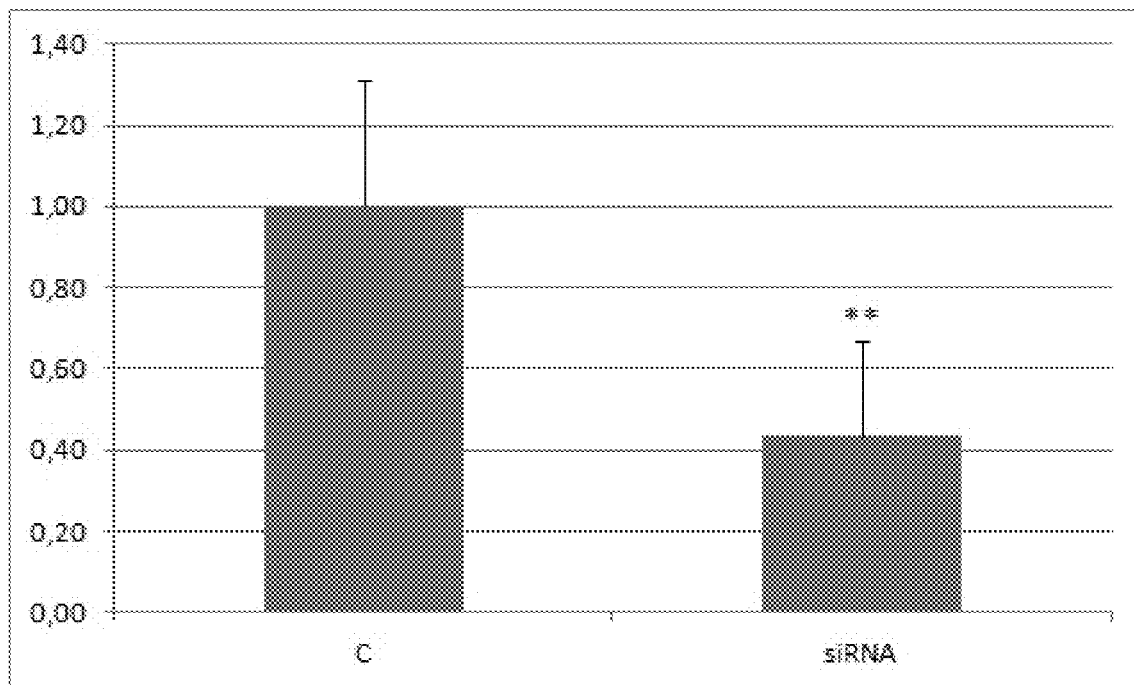
Figure 4B:
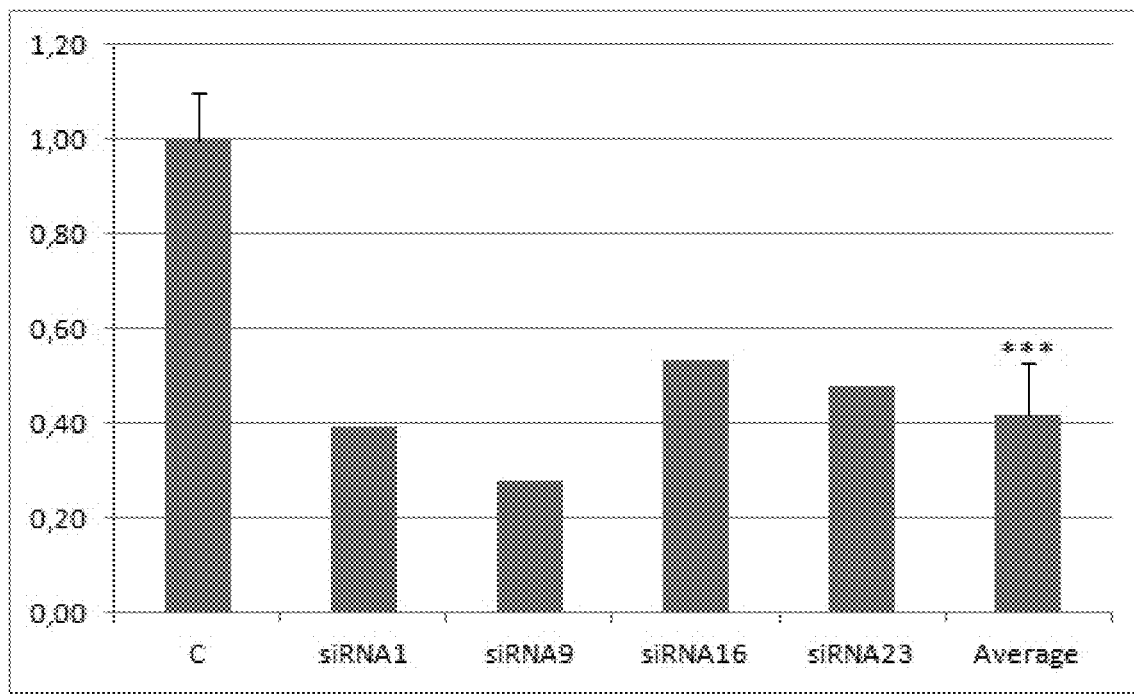

FIGS. 4A and 4B. Down-regulation of sweat-production in humans using topical siRNA (s7635, Ambion) administration as disclosed in Example 2. A: Bars illustrate the relative average sweat production on forearms without siRNA administration ("C"; right forearm used as a control) and after siRNA administration ("siRNA"; left forearm), respectively. ; p<0.01 (Student's t-test). The results are based on six measurements at day 1, 9 and 16 in two adult individuals. siRNA was administrated on left forearm day 0, 1 and 9. B: Bars illustrate the relative sweat volumes in one test subject. The average sweat volume of the control arm ("C") and four individual measurements on the left "test-arm" at day 1, 9, 16 and 23 ("siRNA1-23"). siRNA was administrated at day 0, 1 and 9. The average of the four measurements on the test-arm is also shown ("Average"). *; p<0.001 (Student's t-test).

DETAILED DESCRIPTION OF PREFERRED EMBODIMENTS OF THE INVENTION

The present inventor and co-workers have identified individuals with inherited mutations in the ITPR2 gene that predicts a relative or absolute loss of function of ITPR2. Individuals with both ITPR2 alleles mutated present with generalized anhidrosis (lack of sweating) but no other symptoms (FIG. 1). We also showed that, in dermis and epidermis, ITPR2 is predominantly expressed in the basolateral cells ("clear cells") of the secretory part of the sweat gland (FIG. 2). Therefore, it is expected that by down-regulation of ITPR2 mRNA and/or ITPR2 protein levels or function in sweat glands, this will reduce sweat production.

Agents that interact with ITPR2 mRNA may cause down-regulation of this mRNA. We show this using short interfering RNA (siRNA) that specifically targets ITPR2 mRNA. Thus, any molecule (e.g. nucleic acids and their derivatives) that targets ITPR2 mRNA may lead to reduced levels of ITPR2 mRNA and consequently to reduced levels of ITPR2 protein. Based on our findings from humans with ITPR2 mutations associated with anhidrosis, down-regulation of ITPR2 mRNA or ITPR2 protein, directly or indirectly, may be applied to efficiently reduce sweat production. We show that down-regulation of ITPR2 mRNA is possible using siRNA.

This method has recently emerged as a tool to reduce target expression and the approach has led to a promising treatment option in diverse disorders, including skin and muscle diseases (Leachman, 2010; Goemans, 2011; Burnet and Rossi, 2012). Thus, local or systemic administration of siRNA against ITPR2 mRNA may be used to reduce sweat production. Interfering with ITPR2 mRNA or ITPR2 protein levels using any inhibitors or antagonists may be used for a similar effect on sweat gland function and perspiration. In addition, sweat glands have an important role in the regulation of body temperature. Consequently, a systemic interference with ITPR2 mRNA resulting in a generalized and perturbed perspiration may be used to increase body temperature.

Delivery of exogeneous double stranded (ds) RNA is efficient for the silencing of a gene by inducing the degradation of a homologous host RNA. Gene silencing involves degradation of dsRNA into small interfering RNAs (siRNA). Chemical modifications of the siRNA by e.g. a phosphorothioate backbone or 2'-O-methyl substituents prevent degradation and promotes metabolic stability (Burnet and Rossi, 2012). We used three different double stranded RNAs of 21 nucleotides each in order to down-regulate ITPR2 mRNA. The oligonucleotides have a modified backbone and they are complementary to non-overlapping coding sequences of ITPR2 mRNA. The modified siRNAs were shown to independently down-regulate ITPR2 mRNA up to 4-fold and this suggests that any part of the ITPR2 transcript, including the 5' and 3' UTRs, may be suitable target sequences. The in-vivo delivery of siRNA or nucleic acid derivatives for the reduction of ITPR2 mRNA and ITPR2 protein levels can be accomplished through local or systemic administration consistent with previous examples (Leachman, 2010; Goemans, 2011; Burnett and Rossi, 2012). Local administration of the agent may be especially suitable to access the superficial sweat glands with either passive or active transport across epidermis. For this invention, administration of siRNA or antagonist/inhibitor of ITPR2 mRNA can be accomplished similar to the use of a deodorant (e.g. deo-stick, aerosol or liquid), as well as with a cream or an ointment. Transdermal delivery of siRNA against ITPR2 mRNA can be facilitated when mixed with short synthetic peptides (Lin et al. 2012) or by using cationic liposomes in complex with siRNA (Felgner et al. 1987; Gindy et al. 2012).

Yet other enhancers for topical administration and delivery of siRNA against ITPR2 mRNA is the use of different carriers such as poly(amidoamine)s (Arote R B et al. 2012) as well as patches with dissolvable micro-needles prepared with siRNA (Lara M F et al 2012). The siRNA can also be introduced into cells by a genetic vectors, e.g. as discussed by Li and Rossi, Methods Mol Biol. 2008; 433:287-299, whereby the siRNA is produced in the cell.

Another route to reduce ITPR2 function is to interfere with the pore-forming ability or the calcium channel function of ITPR2. Interference with the pore-forming ability can be done by administering a compound blocking ITPR2 tetrameric assembly.

Another route to reduce ITPR2 protein levels is to down-regulate or completely block transcription of the ITPR2 gene. This may be done e.g. by blocking transcription factors, blocking intracellular signaling, blocking enhancer elements, using repressors of transcription, and/or mitigating activators of transcription, preferably specifically for the ITPR2 gene.

Example 1

In Vitro Down-Regulation of ITPR2 mRNA

FIG. 3 show an efficient down-regulation of ITPR2 mRNA using specific siRNAs in a cell tissue culture system using human primary fibroblast cells. Fibroblast cells were cultured in the presence of dsRNA in vivo ready modified, desalted and HPLC purified dsRNAs with 21 nucleotides complementary to exon 9-10 (s7634, Ambion), exon 26 (s7635, Ambion) and exon 30 (s7636, Ambion) of ITPR2 (Table 1). Total RNA was extracted from fibroblast cultures after 48 h. Non-induced cells were used as controls. Quantitative real time PCR shows a 3-4-fold reduction in ITPR2 mRNA levels after induction by siRNA (FIG. 3). Additional sequences in ITPR2 were predicted as suitable for similar knock-down experiments of ITPR2 mRNA (Table 1).

Example 2

Down-Regulation of Sweat-Production in Humans Using Topical siRNA Administration This example shows the reduced sweat production in human subjects after topical administration of siRNA (s7635, Ambion) using iontophoresis. The sweat production after topical administration of siRNA and iontophoresis where measured on the left forearm and the sweat production on the right forearm of the same individual was used as a control, without siRNA administration.

The experiments were performed on two healthy adults age 36 and 54 y.o.a., respectively. Sweat production was measured using a 3700 Webster sweat inducer and the Macroduct sweat collecting system (Wescor) on forearms according to the manufacturer's recommendation. 50 ug of siRNA dissolved in 50 ul of water was administered on the left test-arm at day 0, day 1 and day 9 and covered by a 3 $cm^2$ agarose plug (4% agarose in saline phosphate buffer) and a katode followed by iontophoresis (1.5 mA, 5 min). To obtain measurable volumes of sweat, pilocarpine was then administrated by iontophoresis at the same 3 $cm^2$ area on the test-arm for 5 min., before the collection of sweat for 25 min according to the manufacturer's recommendation (Macroduct sweat collecting system). Similarly, the control arm was subject to pilocarpine administration with iontophoresis for 5 min., immediately before sweat collection for 25 min. The sweat production was measured on both study participants at day 1, 9 and 16 (FIG. 4A) and in one participant also at day 23 (FIG. 4B). In FIG. 4A the "C"-bar illustrates the average of six measurements of the right "control" forearm and is set to 1. The relative average sweat production of the left forearm (test-arm, six measurements) after siRNA administration is shown as the "siRNA"-bar. An almost 60% reduction of sweat volume is observed **; $p<0.01$; Student's t-test.

FIG. 4B illustrates the relative sweat volumes from one individual with average volume of the right "control" forearm (day 1, 9 and 16; "C") and the individual measurements from the left test-arm (day 1, 9, 16 and 23). The average sweat volume of the test-arm from four measurements is illustrated as "Average". ***; $p<0.001$ (Student's t-test). A reduced sweat production is observed at day one after siRNA administration and remains 14 days after the last siRNA administration at day 9.

Example 3

Down-Regulation of ITPR2 Protein siRNA molecules targeting the ITPR2 mRNA are administered to at least one individual as disclosed in Example 2. Skin biopsies are then taken from the test area and the corresponding control area of the same individual. The amounts of ITPR2 protein in biopsies from test area and control area, respectively, are quantified by immunohistochemistry. It is found that the amount of ITPR2 protein is significantly reduced in sweat glands of the test area as compared to the control area.

Optionally, the amounts of ITPR1 protein and ITPR3 protein are similarly measured in biopsies from the test area and control area. It is found that the amounts of ITPR1 and ITPR3 do not significantly differ between the biopsies from the test area and from the control area.

Sequences

Examples of validated siRNA (5' to 3') for ITPR2 mRNA knock-down and predicted target sequences in the ITPR2 gene for mRNA knock-down.

TABLE 1

| Sequences of validated siRNAs | SEQ ID NO |
|---|---|
| s7634: GCUUAAUCCUGAUUAUCGAtt | 1 |
| s7635: GGUGUCUAAUCAAGACGUAtt | 2 |
| s7636: GCGAGAGAGUUGUACAACAtt | 3 |
| Predicted ITPR2 target sequences: | |
| CCAGCAACATAGAGCTTCTTGATAA | 4 |
| GACCTTGCGCCAATCAGCTACTTCT | 5 |
| AAGCATCTTGCAACTGGAAACTATT | 6 |
| GATGATGAAGAAGTTTGGCTCTATT | 7 |
| CAGAAAGCCTCAGTGGAATCCTGTA | 8 |
| CCAGTGGATTTGGACAGCCAAGTTA | 9 |
| CAGTGGATTTGGACAGCCAAGTTAA | 10 |
| CAGACATTCAGTGTCTGCTGGATAA | 11 |
| CACATGAGTCTAATGGGATTGATAT | 12 |
| CGGTTTCATTTGAGGAGCACATTAA | 13 |

The present invention is not limited to the above-described preferred embodiments. Various alternatives, modifications and equivalents may be used. Therefore, the above embodiments should not be taken as limiting the scope of the invention, which is defined by the appended claims.

REFERENCES

The entire contents of all of the below listed references are incorporated herein by reference.

Arote R B et al. Degradable poly(amido amine)s as gene delivery carriers. Expert Opin Drug Deliv 8, 1237-1246 (2011)

Augin G et al. protein kinase C phosphorylates the inositol 1,4,5-trisphosphate receptor type 2 and decreases the mobilization of Ca2+ in pancreatoma AR4-2J cells. J Endocrin 192, 659-668 (2007)

Burnett J C and Rossi J J. *RNA-based therapeutics: current progress and future*. Chem Biol 19, 60-71 (2012)

Distelhorst C W and Bootman M D. Bcl-2 interaction with the inositol 1,4,5-trisphosphate receptor: Role in Ca2+ signaling and disease. Cell Calcium 50, 234-241 (2011)

Felgner P L et al. Lipofection: a highly efficient lipid mediated DNA-transfection procedure. Proc Natl Acad Sci USA 84, 7413-17 (1987)

Gindy M E et al. Challenges in the pharmaceutical development of lipid based short interfering ribonucleic acid therapeutics. Expert Opin Drug Deliv 9, 171-182 (2012)

Futatsugi A et al. IP3 receptor types 2 and 3 mediate exocrine secretion underlying energy metabolism. Science 309, 2232-2234 (2005)

Goemans N M et al. Systemic administration of PRO051 in Duchenne muscular dystrophy. NEJM 364, 1513-22 (2011)

James, William; Berger, Timothy; Elston, Dirk (eds). Andrews' Diseases of the Skin: Clinical Dermatology. (10th ed.). Saunders. Page 777-8 (2005)

Lara M F et al. Inhibition of CD44 gene expression in human skin models, using self-delivery short interfering RNA administrated by dissolvable microneedle arrays. Hum Gene Therapy 23, 1-8 (2012)

Leachman S A et al. First-in-human mutation-targeted siRNA phase Ib trial of an inherited skin disorder. Mol Therapy 18, 442-6 (2010)

Lin C M et al. A simple, non-invasive and efficient method for transdermal delivery of siRNA. Arch Dermatol Res 304, 139-144 (2012)

Yule D I et al. Linking structure to function: Recent lessons from inositol 1,4,5-triphosphate receptor mutagenesis. Cell Calcium 47, 469-479 (2010)

Zhang S et al. G-protein-coupled receptor kinase-interacting proteins inhibit apoptosis by Inositol 1,4,5-Trisphosphate Receptor mediated Ca2+ signal regulation. J Biol Chem 284, 29158-29169 (2009)

The invention claimed is:

1. A method for treating hyperhidrosis in a subject suffering from hyperhidrosis, comprising administering to said subject suffering from hyperhidrosis a compound capable of at least one of: reducing levels of ITPR2 mRNA; reducing levels of ITPR2 protein; reducing ITPR2 calcium channel formation; reducing ITPR2 calcium channel function, said compound being administered in an amount effective to treat hyperhidrosis.

2. The method of claim 1, wherein said compound is capable of reducing levels of ITPR2 mRNA.

3. The method according to claim 2, wherein said compound is a nucleic acid molecule that targets ITPR2 mRNA.

4. The method according to claim 3, wherein said nucleic acid molecule is an RNA molecule targeting a coding sequence of ITPR2 mRNA.

5. The method according to claim 4, wherein said RNA molecule is a double-stranded RNA molecule.

6. The method according to claim 4, wherein said RNA molecule is an siRNA molecule.

7. The method according to claim 6, wherein said siRNA molecule has a sequence according to any one of SEQ ID NOs:1-3.

8. The method according to claim 6, wherein said siRNA molecule targets a ITPR2 mRNA sequence as set forth in any one of SEQ ID NOs:4-13.

9. The method according to claim 3, wherein said nucleic acid molecule comprises (a) a chemical modification that prevents degradation and promotes metabolic stability or (b) a chemical modification selected from a phosphorothiate backbone and a 2'-O-methyl substituent.

10. The method according to claim 1, wherein said subject is a human.

11. The method according to claim 3, wherein said nucleic acid molecule is delivered to the secretory part of the sweat gland.

12. The method of claim 1, wherein said method comprises administering to said subject a composition comprising a compound capable of at least one of: reducing levels of ITPR2 mRNA; reducing levels of ITPR2 protein; reducing ITPR2 calcium channel formation; reducing ITPR2 calcium channel function and one or more pharmaceutically acceptable carriers and/or excipients, said compound being present in an amount effective to treat hyperhidrosis.

13. The method according to claim 12, wherein said carriers and/or excipients are compounds which facilitate transdermal delivery of said nucleic acid molecule.

14. The method according to claim 13, wherein said carriers and/or excipients are short synthetic peptides, cationic liposomes, lipid-based carriers, poly(amidoamine)s, genetic vectors or dissolvable micro-needles.

15. The method according to claim 12, wherein said composition is for intradermal injection or iontophoresis.

16. The method according to claim 12, wherein said composition is for systemic administration.

17. The method according to claim 12, wherein said composition is for topical administration.

18. The method according to claim 17, wherein said composition is a cream, ointment, stick, aerosol or liquid.

19. The method according to claim 12, wherein said composition is for transdermal delivery of said compound.

20. The method according to claim 19, wherein said composition is a patch.

* * * * *